(12) United States Patent
Zistatsis et al.

(10) Patent No.: US 10,912,666 B2
(45) Date of Patent: Feb. 9, 2021

(54) ENERGY STORAGE DEVICE FOR AN EXOSKELETON

(71) Applicant: University of Washington, Seattle, WA (US)

(72) Inventors: Jessica Zistatsis, Seattle, WA (US); Jeffrey Bergeson, Seattle, WA (US); Alex Gong, Seattle, WA (US); Kira Neuman, Seattle, WA (US); Daniel Parrish, Seattle, WA (US)

(73) Assignee: University of Washington, Seattle, WA (US)

( * ) Notice: Subject to any disclaimer, the term of this patent is extended or adjusted under 35 U.S.C. 154(b) by 425 days.

(21) Appl. No.: 15/836,415

(22) Filed: Dec. 8, 2017

(65) Prior Publication Data

US 2018/0161188 A1    Jun. 14, 2018

Related U.S. Application Data

(60) Provisional application No. 62/431,552, filed on Dec. 8, 2016.

(51) Int. Cl.
*A61H 3/00* (2006.01)
*A61F 5/01* (2006.01)
(Continued)

(52) U.S. Cl.
CPC .............. *A61F 5/0102* (2013.01); *A61F 2/50* (2013.01); *A61H 1/02* (2013.01); *A61H 1/024* (2013.01);
(Continued)

(58) Field of Classification Search
CPC .... A61H 3/00; A61H 3/008; A61H 2003/007; A61H 1/0237; A61H 1/024;
(Continued)

(56) References Cited

U.S. PATENT DOCUMENTS 2,235,047 A    3/1941  Sloan
7,549,969 B2   6/2009  van den Bogert
(Continued)

FOREIGN PATENT DOCUMENTS

CN    202036370 U    11/2011

OTHER PUBLICATIONS

Agrawal, N., et al., "Imaging Data Reveal a Higher Pediatric Stroke Incidence Than Prior US Estimates," Stroke 40:3415-3421, Nov. 2009.
(Continued)

*Primary Examiner* — Alvin J Stewart
(74) *Attorney, Agent, or Firm* — Christensen O'Connor Johnson Kindness PLLC

(57) ABSTRACT

Disclosed herein is a leg exoskeleton configured to aid motion (e.g., walking) of a user in need thereof. In particular, the exoskeleton includes a belt configured to attach the exoskeleton to the waist of a user. The exoskeleton further includes a leg frame configured to attach to at least one leg of the user through a hip attachment mechanism on the belt. Finally, the exoskeleton includes an energy storage subsystem that is configured to store and release energy as the user walks, particularly aiding the user in the forward motion of the leg when walking. Methods of using the leg exoskeleton are also provided.

19 Claims, 11 Drawing Sheets

(51) Int. Cl.
*A61H 1/02* (2006.01)
*A61F 2/50* (2006.01)
*B25J 9/00* (2006.01)

(52) U.S. Cl.
CPC ......... *A61H 1/0237* (2013.01); *A61H 1/0244* (2013.01); *A61H 1/0266* (2013.01); *A61H 3/00* (2013.01); *A61H 3/008* (2013.01); *B25J 9/0006* (2013.01); *A61F 2002/5073* (2013.01); *A61H 2003/007* (2013.01); *A61H 2201/0173* (2013.01); *A61H 2201/0192* (2013.01); *A61H 2201/12* (2013.01); *A61H 2201/14* (2013.01); *A61H 2201/163* (2013.01); *A61H 2201/164* (2013.01); *A61H 2201/165* (2013.01); *A61H 2201/1671* (2013.01); *A61H 2203/0406* (2013.01); *A61H 2205/10* (2013.01)

(58) Field of Classification Search
CPC .......... A61H 1/0244; A61H 2001/0248; A61H 2001/0251; A61H 1/0259; A61H 2201/018; A61H 2201/1445; A61H 2205/06; A61H 2205/10; A61F 2/68; A61F 2002/6818; A61F 2002/6845; A61F 2002/741
See application file for complete search history.

(56) References Cited

U.S. PATENT DOCUMENTS

| | | | | |
|---|---|---|---|---|
| 7,628,766 | B1* | 12/2009 | Kazerooni | A61F 5/00 602/16 |
| 9,675,514 | B2* | 6/2017 | Caires | A61H 3/00 |
| 10,213,356 | B2* | 2/2019 | Glaister | A61H 3/00 |
| 2002/0094919 | A1* | 7/2002 | Rennex | A61F 5/0102 482/124 |
| 2005/0059908 | A1* | 3/2005 | Bogert | A61F 5/0102 601/5 |
| 2007/0027409 | A1* | 2/2007 | Katoh | A61F 5/0102 601/5 |
| 2007/0123997 | A1 | 5/2007 | Herr et al. | |
| 2008/0249438 | A1 | 10/2008 | Agrawal et al. | |
| 2009/0036815 | A1* | 2/2009 | Ido | A61H 1/0237 602/23 |
| 2009/0062884 | A1* | 3/2009 | Endo | B25J 9/0006 607/49 |
| 2010/0094185 | A1* | 4/2010 | Amundson | B25J 9/0006 602/16 |
| 2010/0152630 | A1* | 6/2010 | Matsuoka | A61H 3/008 601/35 |
| 2011/0040216 | A1* | 2/2011 | Herr | A61F 2/68 601/34 |
| 2012/0157894 | A1* | 6/2012 | Hiki | A61H 1/024 601/35 |
| 2012/0271207 | A1 | 10/2012 | Schoen et al. | |
| 2013/0331744 | A1* | 12/2013 | Kamon | A61H 3/00 601/35 |
| 2014/0100492 | A1* | 4/2014 | Nagasaka | A61H 3/061 601/34 |
| 2014/0142475 | A1* | 5/2014 | Goldfarb | A61H 3/00 601/35 |
| 2014/0190289 | A1* | 7/2014 | Zhu | B25J 9/104 74/89.22 |
| 2014/0257160 | A1* | 9/2014 | Garrec | A61F 5/0102 602/23 |
| 2014/0276261 | A1* | 9/2014 | Caires | A61H 1/024 601/33 |
| 2014/0276263 | A1* | 9/2014 | Caires | A61H 3/00 601/34 |
| 2014/0276265 | A1* | 9/2014 | Caires | A61H 3/00 601/34 |
| 2014/0276267 | A1* | 9/2014 | Ayyar | A61F 5/0102 601/35 |
| 2015/0025423 | A1* | 1/2015 | Caires | A61H 1/024 601/35 |
| 2015/0142130 | A1* | 5/2015 | Goldfarb | B25J 9/0006 623/25 |
| 2015/0173993 | A1* | 6/2015 | Walsh | B25J 9/0006 414/4 |
| 2015/0321342 | A1* | 11/2015 | Smith | A61H 3/00 74/490.03 |
| 2016/0107309 | A1* | 4/2016 | Walsh | A61H 3/00 248/550 |
| 2016/0138679 | A1 | 5/2016 | Tesar | |
| 2016/0229065 | A1* | 8/2016 | Angold | B25J 9/0006 |
| 2017/0119613 | A1* | 5/2017 | Roh | B25J 9/0006 |
| 2017/0202724 | A1* | 7/2017 | De Rossi | A61H 3/00 |
| 2017/0209330 | A1* | 7/2017 | Hughes | A61H 3/00 |
| 2017/0340504 | A1* | 11/2017 | Sanz Merodio | A61H 3/00 |
| 2017/0348176 | A1* | 12/2017 | Herr | B25J 9/0006 |
| 2018/0147108 | A1* | 5/2018 | Lee | B25J 9/0006 |
| 2018/0280178 | A1* | 10/2018 | Shimada | A61F 5/0102 |
| 2018/0296422 | A1* | 10/2018 | Sawicki | A61H 1/0244 |
| 2019/0008714 | A1* | 1/2019 | Murakami | A61H 3/00 |
| 2019/0343707 | A1* | 11/2019 | Riener | A61H 1/024 |
| 2020/0060921 | A1* | 2/2020 | Dalley | A61F 5/0123 |
| 2020/0085667 | A1* | 3/2020 | Chen | A61H 3/00 |

OTHER PUBLICATIONS

CFR—Code of Federal Regulations Title 21, FDA, Apr. 1, 2018, <https://www.accessdata.fda.gov/scripts/cdrh/cfdocs/cfcfr/cfrsearch.cfm?fr=890.3475> [retrieved Mar. 27, 2019], 2 pages.
Collins, S.H., et al., "Reducing the Energy Cost of Human Walking Using an Unpowered Exoskeleton," Nature 522:212-215, Jun. 2015; also extended data, 11 pages.
Data and Statistics for Cerebral Palsy, CDC, Mar. 9, 2018, <https://www.cdc.gov/ncbddd/cp/data.html> [retrieved Mar. 25, 2019], 8 pages.
ECFR—Code of Federal Regulations, Government Publishing Office (US), 2016, <https://www.govinfo.gov/app/collection/cfr/2016/>, 7 pages.
ICD-10-CM Codes, "Cerebral Palsy and Other Paralytic Syndromes," ICD10Data.com, 2019, 5 pages.
Medical Device Exemptions 510(k) and GMP Requirements, FDA, Mar. 25, 2019, <https://www.accessdata.fda.gov/scripts/cdrh/cfdocs/cfpcd/315.cfm> [retrieved Mar. 25, 2019], 2 pages.
National Vital Statistics System (NVSS), National Center for Health Statistics, Feb. 21, 2019, <https://www.cdc.gov/nchs/nvss/births.htm> [retrieved Mar. 25, 2019], 5 pages.
Parent, S., et al., "Spinal Cord Injury in the Pediatric Population: A Systematic Review of the Literature," Journal of Neurotrauma 28:1515-1524, Aug. 2011.
Shamaei, K., et al., "Preliminary Investigation of Effects of a Quasi-Passive Knee Exoskeleton on Gait Energetics," Proceedings of the 36th Annual International Conference of the IEEE Engineering in Medicine and Biology Society, Aug. 26-30, 2014, Chicago, pp. 3061-3064.
Van Dijk, W., et al., "A Passive Exoskeleton With Artificial Tendons," Proceedings of the 2011 IEEE International Conference on Rehabilitation Robotics, Rehab Week Zurich, Jun. 29-Jul. 1, 2011, ETH Zurich Science City, Switzerland, 6 pages.

* cited by examiner

ENERGY STORAGE DEVICE FOR AN EXOSKELETON

CROSS-REFERENCE TO RELATED APPLICATION

This application claims the benefit of U.S. Provisional Application No. 62/431,552, filed Dec. 8, 2016, the disclosure of which is hereby expressly incorporated by reference in its entirety.

BACKGROUND

Children with gait disorders, particularly those with neurological conditions such as cerebral palsy or stroke, are developmentally delayed and may exhibit a number of abnormalities in their gait. Individuals with gait disorders often exhibit limited walking time outside of therapy that can affect their rehabilitation and daily life. The amount of walking time an individual experiences when starting to walk is especially important for developing proper gait patterns. Although therapeutic methods are available, most are either expensive or required supervision by a trained clinician. As such, these individuals do not get the proper amount of walking time outside of therapy to support long-term mobility and quality of life. There is a need for a way to increase walking time for people with gait disorders to establish efficient gait patterns.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a leg exoskeleton is provided. In one embodiment, the exoskeleton includes:

a belt configured to attach to a user, the belt comprising a hip attachment mechanism configured for removably coupling a leg frame to a hip of the user;

the leg frame having a proximal portion and a distal portion, the leg frame configured for extending along a length of the user's leg when the user dons the leg exoskeleton with the proximal portion coupled to the hip attachment mechanism at a hip joint and the distal portion coupled to the user at a location distal to the user's knees; and an energy storage subsystem coupled to the hip attachment mechanism and the leg frame, the energy storage subsystem comprising:

an exotendon extending from the hip attachment to the distal portion of the leg frame, the exoskeleton configured to store energy as the user's leg moves posteriorly and release stored energy to aid the user with moving the leg anteriorly, a biasing member disposed along the exotendon, the biasing member configured for storing and releasing energy, and a two☐way ratchet disposed along the exotendon in proximity to the hip attachment mechanism, the two☐way ratchet configured for adjusting tension in the biasing member.

In another aspect a method of using the leg exoskeleton as described herein is provided, the method including:

attaching the leg exoskeleton to at least one leg of a user; and assisting the user in movement of the at least one leg.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5A: Testing configuration with the thigh strut fixed to the table and the foot and tibia free to swing about the knee joint. FIG. 5B: The leg completely extended, preparing to release. FIG. 5C: The foot freely swinging. FIG. 5D: The foot at rest after the pendulum test.

DETAILED DESCRIPTION

Figure 1A:
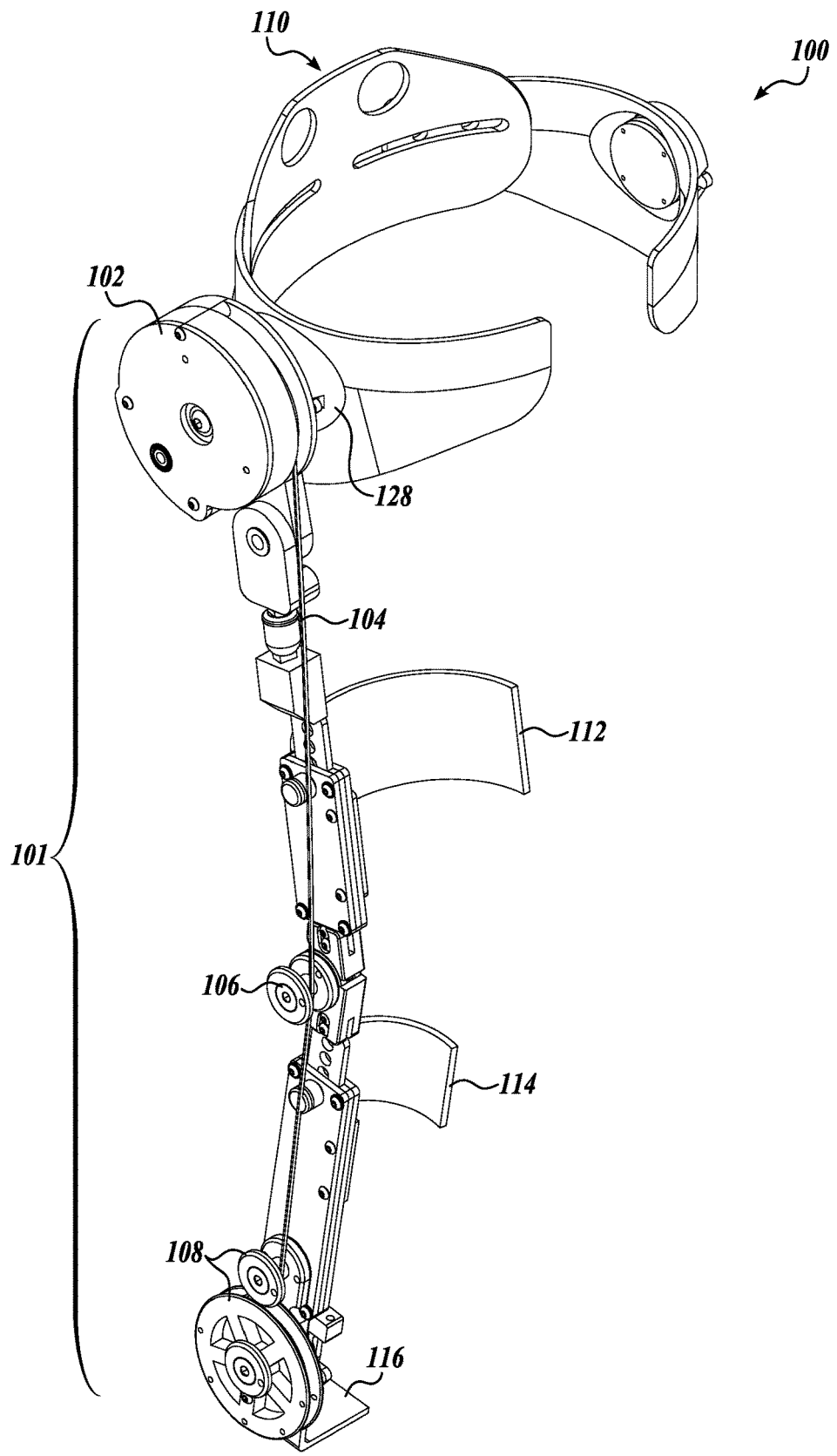
FIG. 1A is a perspective view of a representative leg exoskeleton in accordance with the embodiments disclosed herein.

In order to address the perceived needs of pediatric patients with gait disorders, six core functions were identified as follows: patients can easily don/doff the device, the device promotes fluid movement, the device is durable, the device increases the patient's walking time outside of therapy, the device fails in a predictable manner, the device does not scratch or break skin, and the device can be easily adjusted. Current devices used to treat pediatric gait disorders vary based on the type of disorder. For example, the Bioness L300 helps only with foot drop and does not address fluid movement, whereas the Kickstart, by Cadence Biomedical, addresses all of the core functions identified except adjusting for children ages three to six years old. In view of these requirements the inventors developed a passive pediatric exoskeleton. The disclosed exoskeleton features an innovative ratcheting hip pulley that houses a passive energy storage device in combination with an exotendon running from the hip to ankle pulley to assist with hip flexion and ankle dorsiflexion. It can be used unilaterally or bilaterally based on the patient's condition. In order to test whether the exoskeleton was successful, both standardized testing (three-point bend test) and developed tests (comfort and fit, range of motion, adjustment of leg members, scratch and pendulum tests) were performed.

The disclosed exoskeleton exceeds other exoskeletons in today's market due to its ability to passively promote fluid movement and adjust size and fit for the target age range of 3-6 years old. The disclosed exoskeleton seeks to enable children born with gait disorders to walk more with proper gait patterns while reducing rehabilitation time.

The disclosed exoskeleton seeks to meet a crucial need in the development and quality of life for children born with gait disorders.

In one aspect, a leg exoskeleton is provided. In one embodiment, the exoskeleton includes:

a belt configured to attach to a user, the belt comprising a hip attachment mechanism configured for removably coupling a leg frame to a hip of the user;

the leg frame having a proximal portion and a distal portion, the leg frame configured for extending along a length of the user's leg when the user dons the leg exoskeleton with the proximal portion coupled to the hip attachment mechanism at a hip joint and the distal portion coupled to the user at a location distal to the user's knees; and an energy storage subsystem coupled to the hip attachment mechanism and the leg frame, the energy storage subsystem comprising:

an exotendon extending from the hip attachment to the distal portion of the leg frame, the exoskeleton configured to store energy as the user's leg moves posteriorly and release stored energy to aid the user with moving the leg anteriorly, a biasing member disposed along the exotendon, the biasing member configured for storing and releasing energy, and a two☐way ratchet disposed along the exotendon in proximity to the hip attachment mechanism, the two☐way ratchet configured for adjusting tension in the biasing member.

Embodiments of the leg exoskeleton will now be described with reference to the FIGURES. Referring first to FIG. 1A, a representative leg exoskeleton 100 is illustrated. The exoskeleton 100 is unilateral, configured to attach to one leg of a user.

The exoskeleton 100 includes a belt 110 that is configured to secure to the hip/waist of a user so as to position the exoskeleton 100 properly in relation to the user's body. The belt 110 includes a back plate 111 and two hip pieces 113. Each hip piece 113 is independently secured to the back plate 111 using binding barrels and screws. The hip pieces 113 may slide medially or laterally along the horizontal slots in the back plate 111 and then be fastened down where necessary to adjust the width of the belt 110. The adjustable width range accommodates the waist size of 5th percentile 3-year olds to 95th percentile 6-year olds. In one embodiment, there is a Velcro strap fastened to the front of the belt 110 and the entire belt 110 is lined with foam for comfort, as pictured in FIGS. 8A and 8B.

A leg frame 101 is attached to the belt 110 and is configured to secure to the user's leg and to assist moving the leg when walking. The leg frame 101 includes an energy storage subsystem 102 configured to store and release energy during the walking motion. As part of the energy storage subsystem 102, an exotendon 104 runs the length of the leg frame 101, from a proximal end secured in the energy storage subsystem 102, through a knee pulley 106, and terminating in an ankle pulley 108. During movement of the leg, the exotendon 104 transfers motion of the leg frame 101 into stored energy in the energy storage subsystem 102 when the leg moves posteriorly and releases energy when the leg moves anteriorly.

The leg frame 101 is attached to the user's leg via an upper cuff 112, a lower cuff 114, and a foot plate 116. Cushions are attached to each cuff and secure the device to the body with Velcro straps. The foot plate 116 rests outside the user's shoe and attaches to the foot with Velcro straps for clinical fitting and training environments. For a user's home and community environment, the foot plate 116 is to be replaced with a custom foot orthosis that sits inside the user's shoe for improved performance and fit.

Figure 8A:
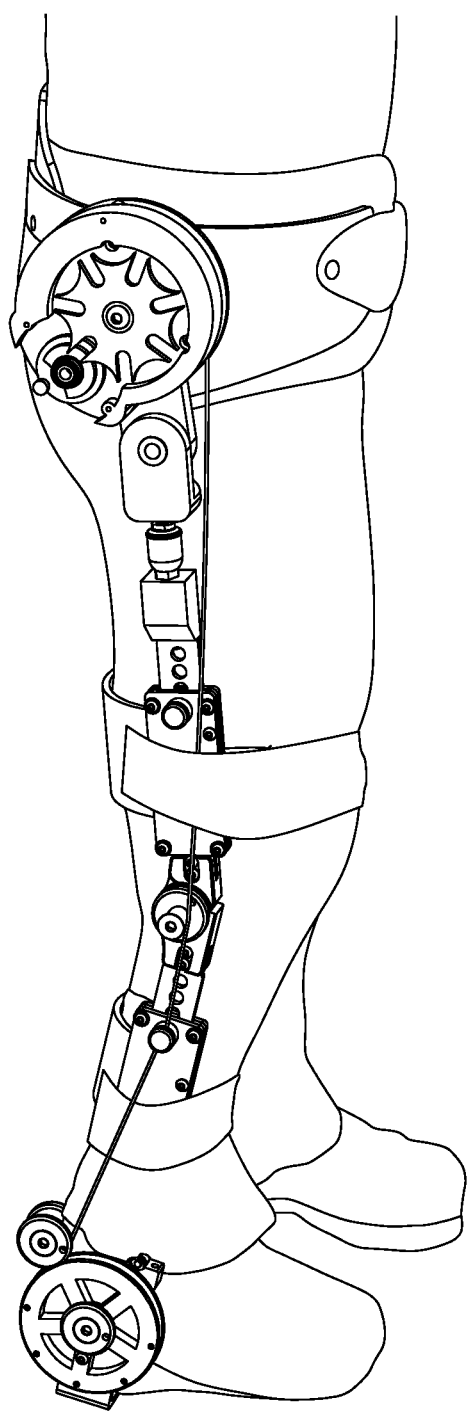
FIGS. 8A and 8B: Photographs of an exemplary exoskeleton worn by a child.
Figure 8B:
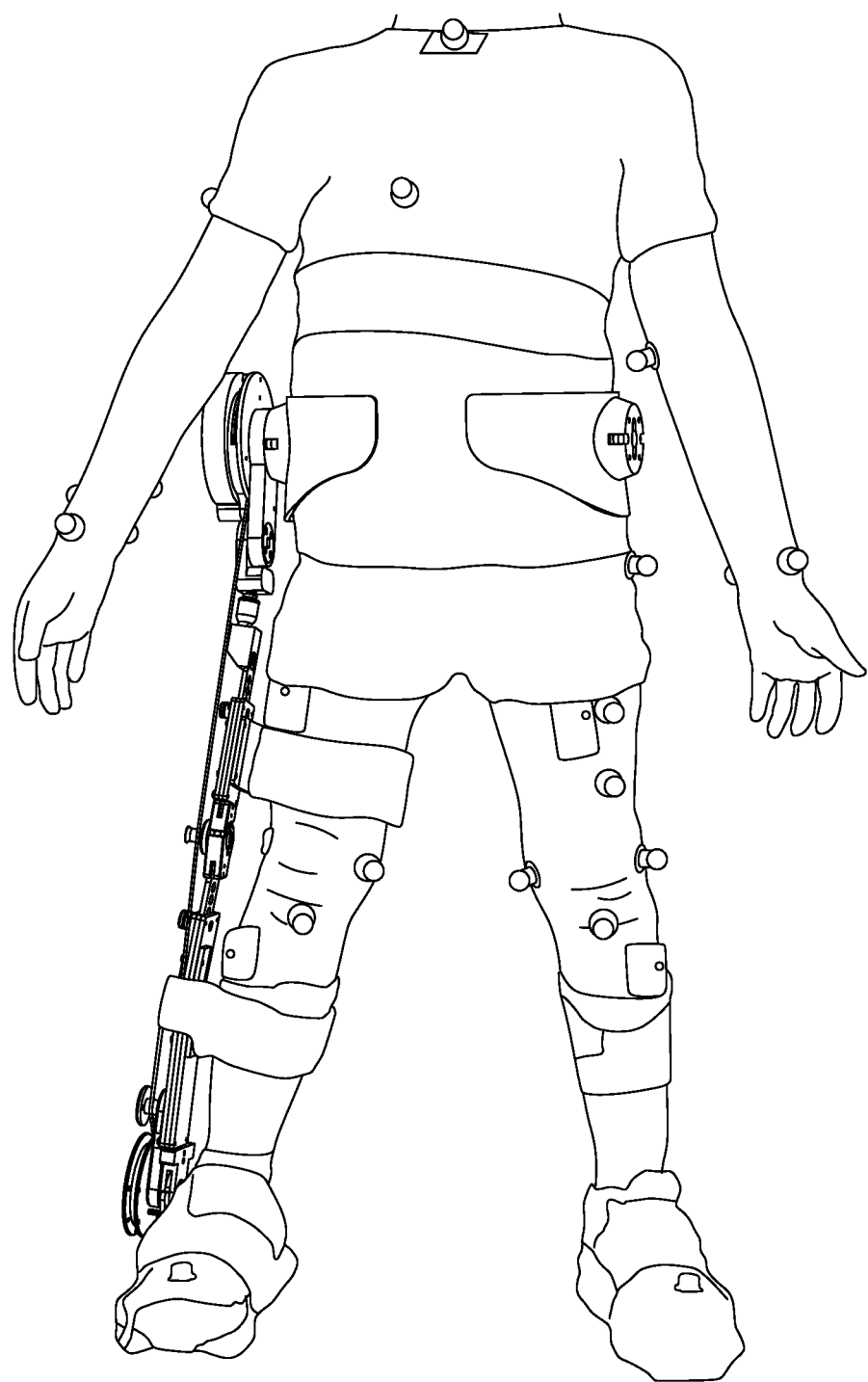

FIGS. 8A and 8B provide further context to the description of the leg exoskeleton by illustrating an exemplary exoskeleton worn by a child.

Figure 1B:
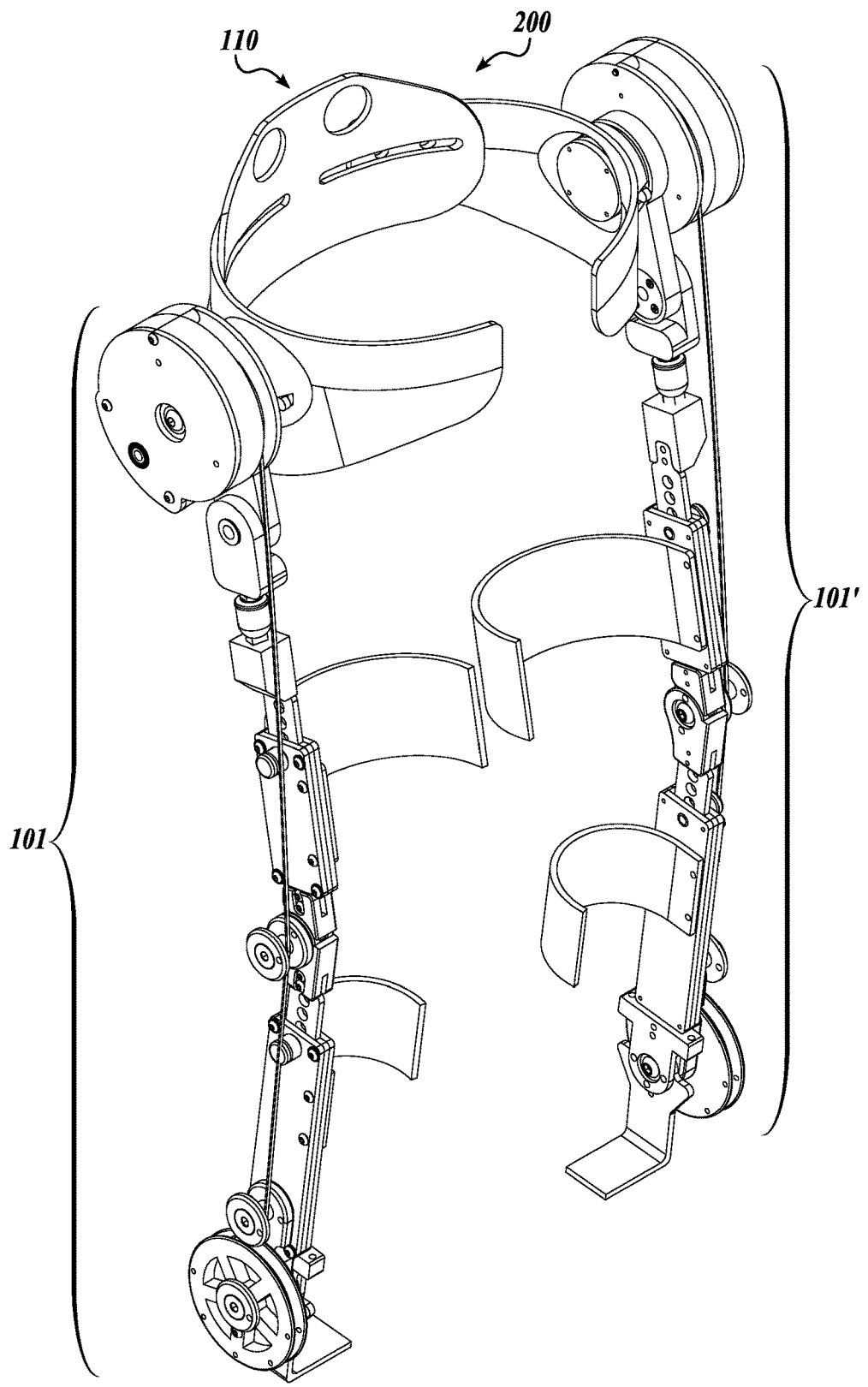
FIG. 1B is a perspective view of a bilateral leg exoskeleton in accordance with the embodiments disclosed herein.

Referring to FIG. 1B, another embodiment of the leg exoskeleton 200 is illustrated, with this embodiment including a first leg brace 101, as described previously and illustrated here as configured to attach to a right leg of a user, as well as a second leg brace 101' similar in composition to the first leg brace 101 but configured to attach to the other leg of the user, the left leg as illustrated here. Accordingly, in one embodiment the leg frame is a first leg frame 101 configured for extending along a length of the user's first leg, and wherein the leg exoskeleton 200 comprises a second leg frame 101' configured for extending along a length of the user's second leg. In yet a further embodiment, the energy☐storage subsystem is a first energy☐storage subsystem coupled to the hip attachment mechanism and the first leg frame, and wherein the leg exoskeleton comprises a second energy☐storage subsystem coupled to the hip attachment mechanism and the second leg frame. It should be appreciated that the energy-storage subsystem ratchet on each leg is independently adjustable, which allows for a broad range of applications for children with differing levels of impairment in each leg.

Figure 2A:
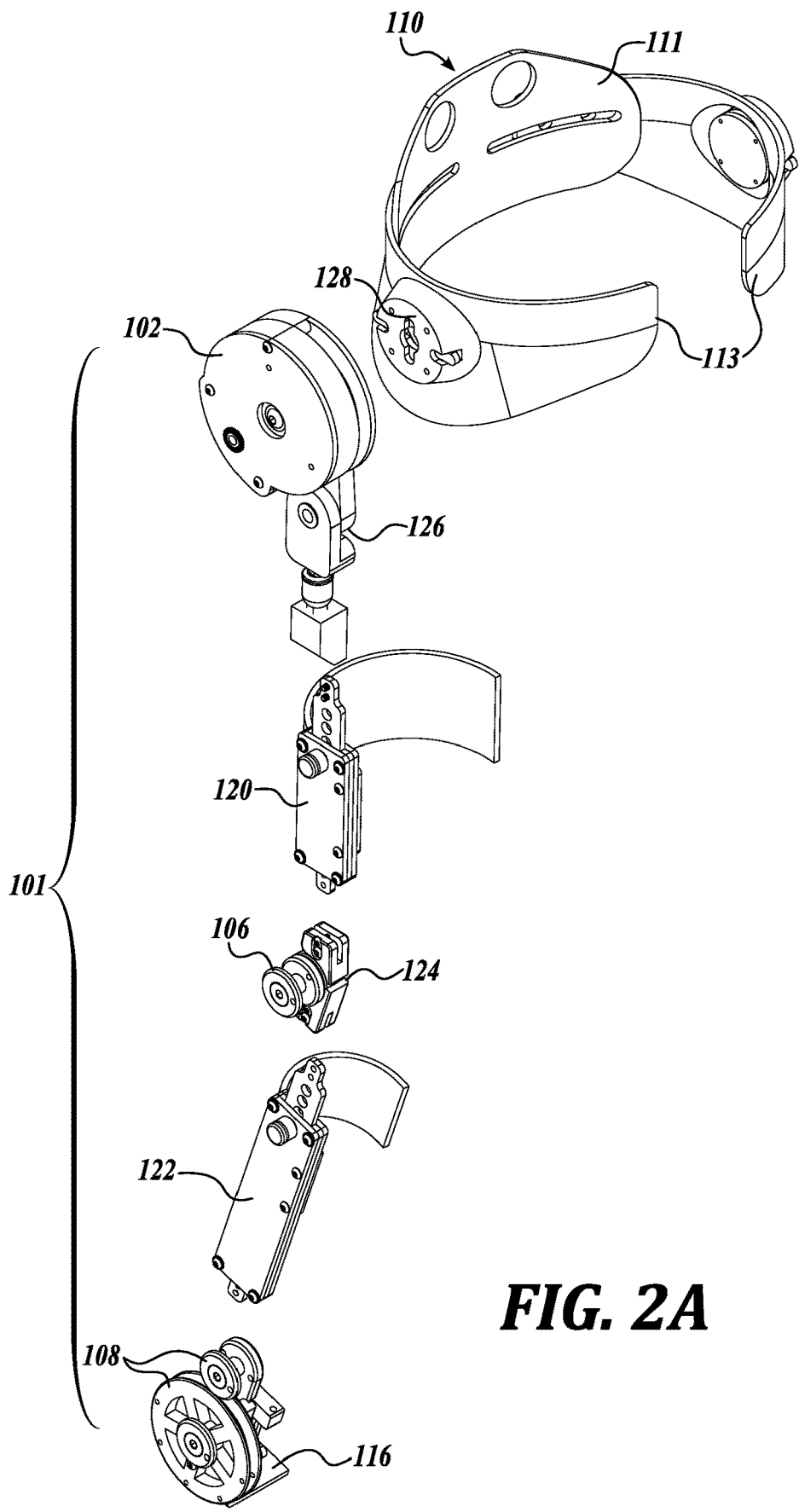
FIG. 2A is a partially exploded view of a leg exoskeleton of FIG. 1A.

FIG. 2A is an exploded view of a unilateral exoskeleton of the type illustrated in FIG. 1A. The components of the leg frame 101 can be seen more clearly in FIG. 2A, including the mating between the portions of the leg frame 101. Beginning at the top, the energy storage subsystem 102 is at the top of the leg frame 101 and includes a hip joint 126 that provides a range of motion at the top of the user's leg. An upper leg member 120 descends from the hip joint 126 and is attached using a length-adjustable system that will be described in greater detail below.

The upper leg member 120 is connected to the knee joint 124, which provides a range of motion to the user's leg at the knee and also supports the knee pulley 106 that guides the exotendon (not illustrated in FIG. 2A for purposes of clarity).

Figure 4:
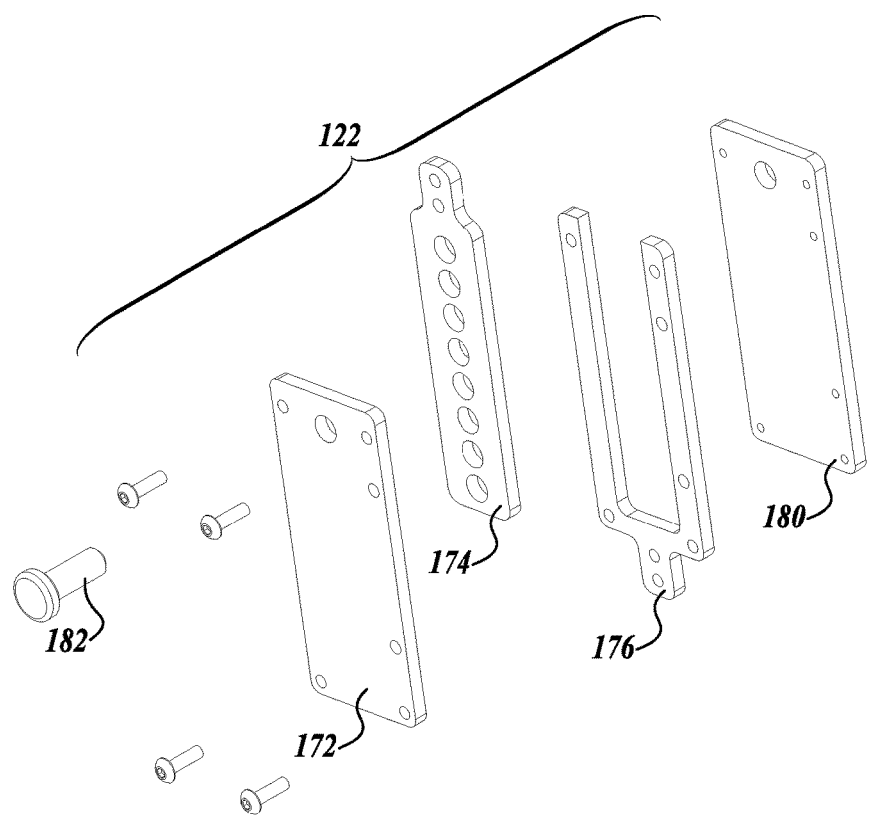
FIG. 4: Exploded view of the adjustable leg struts showing, from left to right, the fasteners, cover plate, a sliding bar with evenly spaced holes for setting leg length, and a tuning fork to guide the sliding bar.

The lower leg member 122 connects the knee joint 124 to the foot plate 116 and supports the user's foot as well as the ankle pulley 108. The lower leg member 122 is similar in design to the upper leg member 120 in that it is adjustable in length so as to customize fit to a particular user's leg dimensions. Accordingly, in one embodiment the leg frame 101 has an adjustable length. FIG. 4 illustrates the construction of the representative lower leg member 122, which includes a front plate 172, a back plate 180, a central support 176, and a positioning plate 174 having a plurality of holes, into which a positioning pin 182 is placed to adjust the distance between the knee joint 124 and the ankle pulley 108. The upper leg member 120 is similarly constructed and adjustable.

Figure 2B:
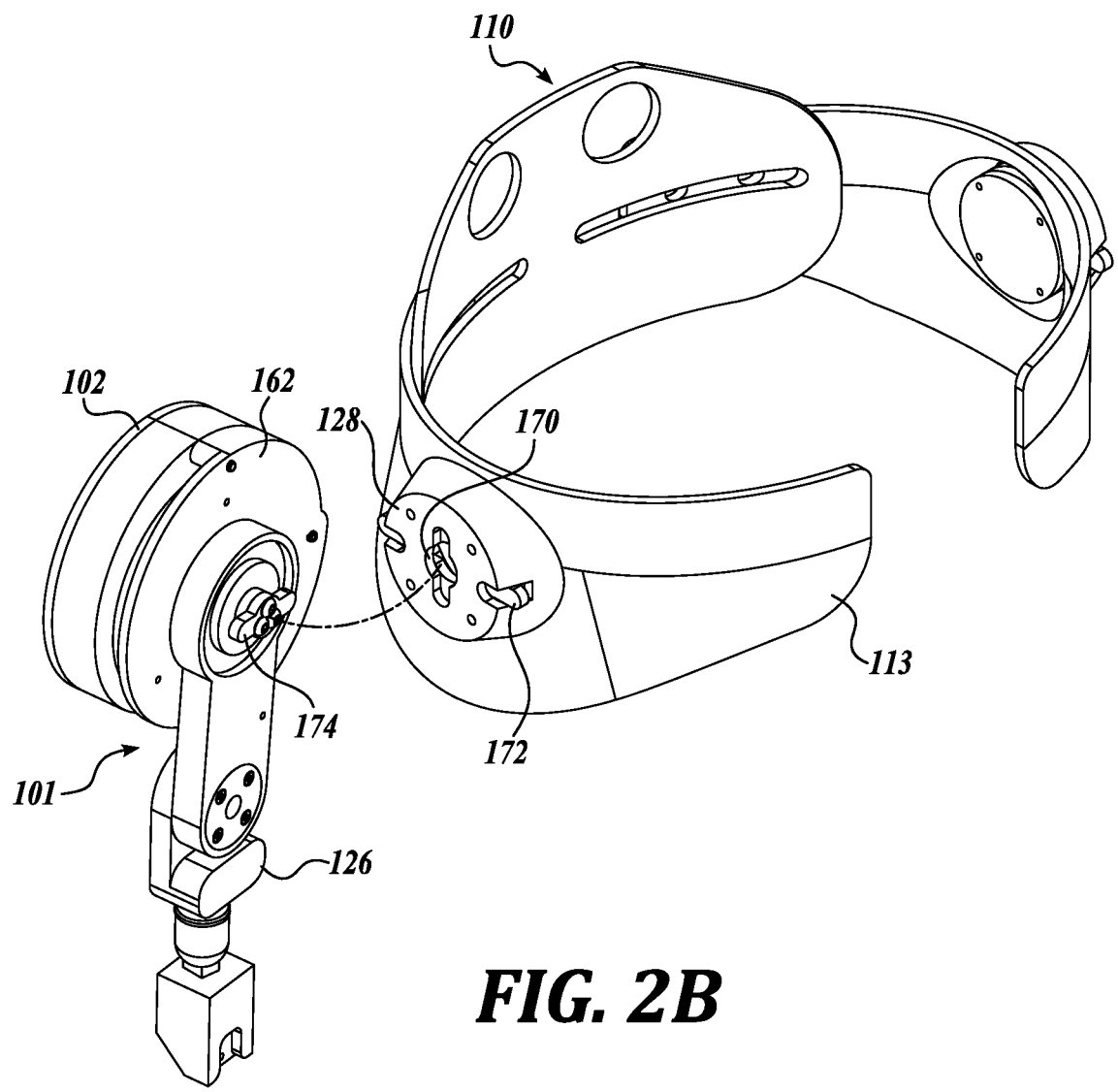
FIG. 2B is a close-up view of the components of the hip attachment mechanism.

In FIG. 2B, the leg frame 101 is illustrated as releasably secured to a hip attachment mechanism 128. In particular, a spring-loaded system that requires pushing on two tabs 172 to release the leg frame 101 from the hip attachment mechanism 128 is illustrated. A spring within the hip attachment mechanism (not illustrated) is compressed while a winged projection 174 attached to the hip case 162 of the leg frame 101 is secured to the hip attachment mechanism 128. To release, two tabs 172 are pressed medially to further compress the spring and release pressure off the winged projection 174. While this component is engaged, the hip case 162 is rotated 90 degrees such that winged projection 174 on the medial side of the hip case are aligned with the vertical opening 170 of the hip attachment mechanism 128.

Figure 3A:
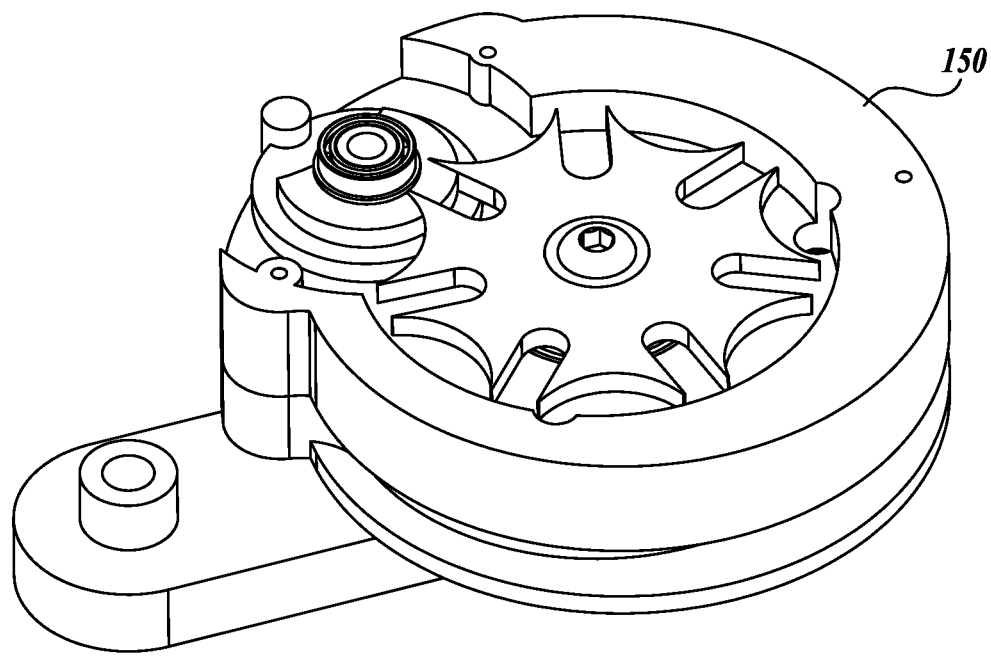
FIG. 3A: A hip pulley featuring a Geneva mechanism, as used in certain embodiments disclosed herein.
Figure 3B:
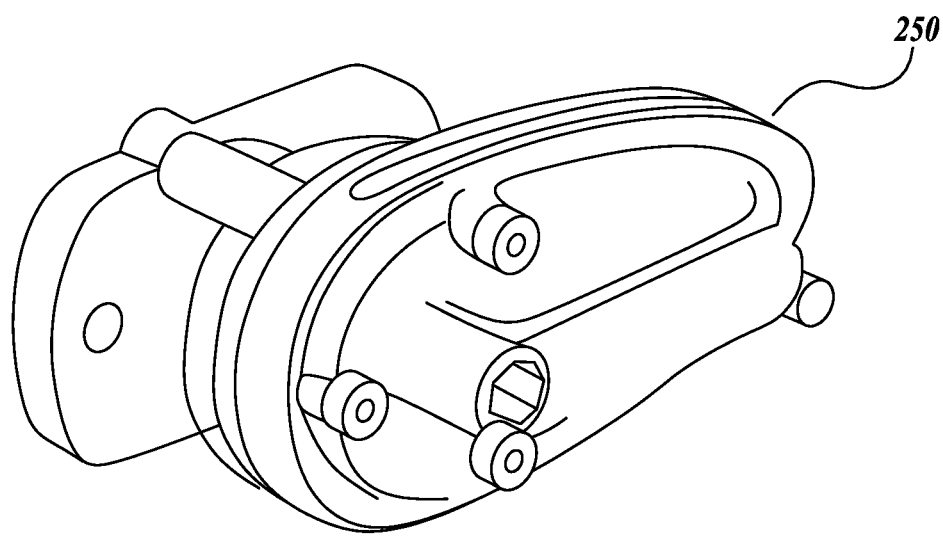
FIG. 3B: A hip pulley featuring a cam design, as used in certain embodiments disclosed herein.

The energy storage subsystem 101 includes a two-way ratchet that is configured for adjusting tension in the biasing member. Turning now to FIGS. 3A and 3B, the two-way ratchet of the energy storage subsystem 102 will be described further. As noted previously, the disclosed exoskeleton 100 utilizes an exotendon 104 and an energy storage subsystem 102 to store energy and assist the swing phase of walking. The force applied is controlled by the tension in the exotendon 104 due to the stretch of a spring, which is adjusted using a ratcheting pulley found in energy storage subsystem 102 (as will be illustrated and described further). The pulley in the energy storage subsystem 102, along with those at the knee 106 and ankle 108, ensure that the force is properly applied to achieve a natural gait pattern.

Two designs are considered for the energy storage subsystem 102, each featuring a different method for energy storage and adjusting the exotendon 104 force. In one embodiment a Geneva mechanism for ratcheting the tension with an internal torsional spring is used as the energy storage subsystem. An exemplary Geneva mechanism 150 is pictured in FIG. 3A. This embodiment removes any need for a linear spring hanging near the lower leg and therefore is safer and less likely to fail due to the contained nature of the internal torsion spring.

In another embodiment, as illustrated in FIG. 3B, a cam 250 is used at the hip contact of the exotendon. This reduces bulk at the hip, but still allows for the necessary radius at the critical point.

In certain embodiments, the biasing member is disposed along the exotendon and is configured for storing and releasing energy. An example of a biasing member is a spring. Referring to FIG. 1A, the biasing member is disposed within the energy storage subsystem 102 case. Accordingly, in one embodiment the biasing member is disposed at least partially within energy storage subsystem 102.

Figure 3C:
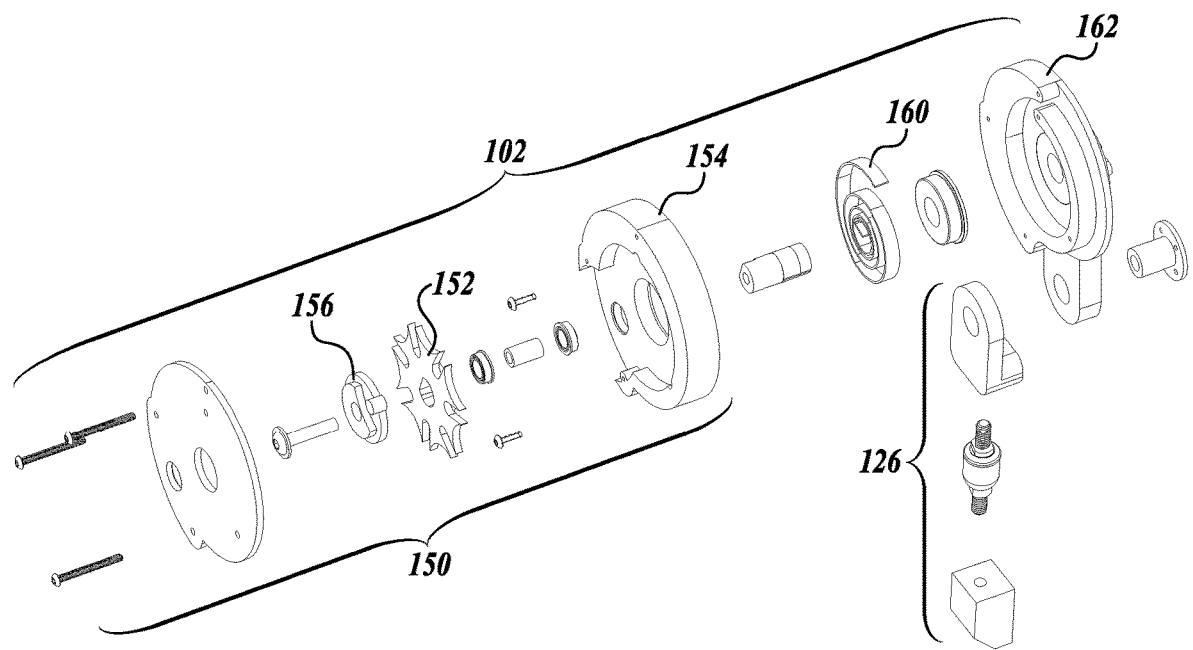
FIG. 3C: Exploded view of a hip pulley mechanism of FIG. 3A featuring a Geneva mechanism, as used in certain embodiments disclosed herein.

Referring now to FIG. 3C a specific embodiment of the energy storage subsystem 102 will be described. In this embodiment the biasing member is a spring 160 disposed within the energy storage subsystem 102 case. In this embodiment the spring is a spiral torsion spring. In this embodiment the spiral torsion spring 160 is enclosed within a case 162 along with the ratcheting mechanism 150 in an adjacent case 154. The ratcheting mechanism 150 is a two-way ratchet that includes a Geneva mechanism with gear 152 and turning pin 156 disposed in a frame 154. As the Geneva mechanism rotates it is coupled to the spring 160, which in turn is attached to the proximal end of the exotendon to provide tension. In one embodiment the spring has an instantaneous stiffness range of 87 N/m to 2977 N/m.

The hip joint 126 extends from the energy storage subsystem 102 in the illustrated embodiment.
Methods of Using the Exoskeleton Methods of using the disclosed leg exoskeletons are also provided. Accordingly, in another aspect a method of using the leg exoskeleton as described herein is provided, the method including:

attaching the leg exoskeleton to at least one leg of a user; and assisting the user in movement of the at least one leg.

In one embodiment the method includes assisting the user in movement of the at least one leg comprises storing energy in the biasing member when the at least one leg swings posteriorly during walking and releasing energy from the biasing member when the at least one leg swings anteriorly during walking, thereby assisting the user with movement forward.

In one embodiment the method further includes pre-biasing the biasing member so as to provide stored energy in the biasing member before any movement of the user.

In one embodiment the leg exoskeleton is attached to two legs of the user and assist in movement of the two legs.

In one embodiment the method further includes adjusting the length of the leg frame in order to fit the user prior to movement.

In one embodiment the biasing member is a spiral torsion spring attached to the proximal end of the exotendon.
Pulley Optimization The chosen design for storing and releasing energy to assist with correcting gait patterns results from two minimizations that were used for calculating several of the variables in a single exotendon system. These calculations use healthy gait data and variables such as pulley radii, spring constant, and initial spring displacement to determine the average residual joint moment ($C_{mom}$) and the average mechanical power generated by the residual joint moments ($C_{pow}$). By minimizing $C_{mom}$ and $C_{pow}$, theoretically the strength and power required for walking is made as low as possible for normal walking patterns. The minimization equations, variables, and explanations can be found in the Equation section below. The method for minimization was simulated annealing.

The idea that drives the disclosed exoskeleton is that minimizing either $C_{mom}$ or $C_{pow}$ will encourage a normal walking pattern by reducing the energy required. This will allow for a normal gait cycle even with reduced limb strength. The downside of these calculations is that some of the assumptions used are unrealistic. For instance, the exotendon is assumed to be directly attached to the bone, which is not possible for a non-intrusive device. Assumptions like this can lead to optimization values that are not necessarily physically possible, unless reasonable limits are placed on the minimization.

In order to run these minimizations, first the adult data for a healthy gait pattern was adjusted so that the values reflected that of a child. Specifically, two sets of data were created based on the adult data, one for the 95th weight percentile of six-year-old children and one for the 5th weight percentile of three-year-old children. These ranges were selected because the target population for the pediatric exoskeleton is children aged three to six based on clinical need. By running the minimization for these two sets of data, a range of optimized values was generated to define the exotendon system.

The second step required for the minimizations was to recreate the equations in a computational program. This was performed in Mathematica (Wolfram Research, Champaign, Ill.).

During the initial run of the optimization, the calculated results were found to be impossible values due to the radius at the ankle pulley being larger than the distance from the center of the ankle to the ground. The optimization was changed so that the pulleys cannot exceed this maximum value. Unfortunately, the distance from the ankle center axis to the ground for the smallest child could not be found using modeling. It was instead based off of the optimization of an adult population, which has about twice the leg length of our smallest children's population. The adult-calculated radius of the ankle pulley was 54 mm; therefore, the ankle pulley radius of the exemplary exoskeleton was set to 27 mm. Limits were also set on the hip pulley in a similar way. The adult hip pulley radius was 67 mm, so a limit of 34 mm was set for the exemplary children's exoskeleton.

Lastly, a limit on the size of the spring constant was placed because a maximum constant of approximately 700 N/m is possible for a normal extension spring that would fit within the leg length of the smallest child envisioned. In addition to this, the adult-based modeling yielded an incredibly high spring constant that was not realistic for manufacturing, which resulted in putting a limit on the spring constant in order to find more useful values. Ultimately an extension spring would not be used in the disclosed exoskeleton, but the optimized spring constant value in this case informs design parameters for the aforementioned spiral torsion spring.

After optimizing with the addition of component limits mentioned above, the optimal values for the ankle pulley radius, hip pulley radius, and spring constant were determined to be −27 mm, 34 mm, and 700 N/m, respectively. The negative radius of the ankle pulley indicates the exotendon should wrap around the pulley posteriorly, as opposed to a positive radius indicating wrapping the pulley anteriorly. The radius of the knee pulley changes depending on the value minimized and population, as well as the spring extension from slack length, as shown in Table 1.

TABLE 1

Knee pulley radius as a function of parameter minimized and slack length

| Population Minimization | Slack Length (mm) | Radius of Knee Pulley (mm) |
|---|---|---|
| Small $C_{pow}$ | −31 | 27 |
| Large $C_{pow}$ | −104 | 23 |
| Small $C_{mom}$ | −33 | 7 |
| Large $C_{mom}$ | −94 | 17 |

However, the slack length changes very little between minimizations, and only with different populations. This means that the pre-loading (initial stretch induced by ratcheting the Geneva mechanism before a user walks with the exoskeleton) for different aged users will be different, but will not be significantly different depending on whether it is designed for minimizing residual moment or minimizing residual power. The results for the knee radii suggest that there is a specific sized pulley that will be optimal for an individual based on their size. However, for the scope of this example, an ideal pulley would be "one size fits all" so a knee pulley radius of 4.76 mm was used, a value that aligns with the knee pulley radius of the adult exoskeleton.

In conclusion, after optimizing data for the target age group, dimensions for the device were determined to fabricate an exemplary prototype.

For the optimal pulley radii values, the pullies induce moment values of (where moment=exotendon force*pulley radius and exotendon force is a function of spring stiffness and slack length from Table 1):

Hip moment: 0.025-12 Nm
Knee moment: 0.0035-1.60 Nm
Ankle moment: −0.02--9.0 Nm

In view of these optimal values, in one embodiment the radius of the hip pulley is in the range of 5-50 mm. In one embodiment the radius of the knee pulley is in the range of 2-40 mm. In one embodiment the radius of the ankle pulley is 2-60 mm.

Minimization Equations and Variables with Explanations

There are three kinds of variables in the following equations: data variables, place holder variables, and system variables. Data variables are based on specific information at different points in the gait cycle. Placeholder variables are calculated sets of values that are used as intermediate steps in the calculations. System variables are the output values that determine different aspects of the exotendon system.

The Data variables are as follows:
$JA_1$=Joint angle of the ankle during a specific time in the gait cycle
$JA_2$=Joint angle of the knee during a specific time in the gait cycle
$JA_3$=Joint angle of the hip during a specific time in the gait cycle
$JM_1$=Joint Moment of the ankle at a specific time in the gait cycle
$JM_2$=Joint Moment of the knee at a specific time in the gait cycle
$JM_3$=Joint Moment of the hip at a specific time in the gait cycle The placeholder variables are as follows:
EF=Exotendon Force
$RM_1$=Residual Moment at the ankle
$RM_2$=Residual Moment at the knee
$RM_3$=Residual Moment at the hip
$AV_1$=Angular Velocity at the ankle
$AV_2$=Angular Velocity at the knee
$AV_3$=Angular Velocity at the hip
$RP_1$=Residual Power at the ankle
$RP_2$=Residual Power at the knee
$RP_3$=Residual Power at the hip The System variables are as follows:
$R_1$=pulley radius at the ankle
$R_2$=pulley radius at the knee
$R_3$=pulley radius at the hip
K=spring constant
$L_s$=spring extension away from slack length Equations:
Equation 1 is used to calculate the force in the exotendon for specific time in the gait cycle.

$$EF = \text{Max}\left[0, K\frac{(-(JA_1 * R_1) - (JA_2 * R_2) - (JA_3 * R_3)) * \frac{\pi}{180} - L_S}{1000}\right] \quad \text{Eq. 1}$$

Equations 2-4 are used to calculate the residual moments at the separate joints.

$$RM_1 = \frac{JM_1 - (R_1 * EF)}{1000} \quad \text{Eq. 2}$$

-continued $$RM_2 = \frac{JM_2 - (R_2 * EF)}{1000} \quad \text{Eq. 3}$$

$$RM_3 = \frac{JM_3 - (R_3 * EF)}{1000} \quad \text{Eq. 4}$$

Equations 5-7 calculate the angular velocity at each joint. $t_2$ and $t_1$ refer to two points in time within the gait cycle, which are needed to find the approximate rate of change at the present time in the gait cycle.

$$AV_1 = \frac{(JA_{1t_2} - JA_{1t_1})}{\frac{1}{25}} * \frac{\pi}{180} \quad \text{Eq. 5}$$

$$AV_2 = \frac{(JA_{2t_2} - JA_{2t_1})}{\frac{1}{25}} * \frac{\pi}{180} \quad \text{Eq. 6}$$

$$AV_3 = \frac{(JA_{3t_2} - JA_{3t_1})}{\frac{1}{25}} * \frac{\pi}{180} \quad \text{Eq. 7}$$

Equations 8-10 calculate the residual power at each point.

$$RP_1 = RM_1 * AV_1 \quad \text{Eq. 8}$$

$$RP_2 = RM_2 * AV_2 \quad \text{Eq. 9}$$

$$RP_3 = RM_3 * AV_3 \quad \text{Eq. 10}$$

Equations 11 and 12 minimize the moment and power throughout the gait cycle.

$$C_{mom} = \text{Mean}\left[\frac{|RM_1| + |RM_2| + |RM_3|}{3}\right] \quad \text{Eq. 11}$$

$$C_{pow} = \text{Mean}\left[\frac{|RP_1| + |RP_2| + |RP_3|}{3}\right] \quad \text{Eq. 12}$$

See for reference A. J Van Den Bogert, "exotendons for assistance of human locomotion", *Biomedical Engineering*, vol. 2, no. 17, pp. 1-8, 2003.

Combining the medical needs of children with gait disorders and the gaps in the current solution landscape, a set of core functions most important to the exoskeleton were developed. The exoskeleton must:

Easily be donned/doffed by the patient
Increase walking time outside of therapy
Easily be adjusted or modified for growth (changes in height, waist size)
Promote fluid movement (minimize jerks at the transition between toe off and swing phase)
Be durable
Fail in a predictable manner
Not scratch or break the skin The success of the prototype exoskeleton was determined by testing the device against each specification via the given evaluation methods. The specifications include:

Don/doff and adjust within 5 minutes
Tibial accelerations of −2.09 g peak negative anterior-posterior, 0.90 g peak lateral, and 1.70 g peak axial (herein g refers to acceleration due to local gravity)
Range of Motion: hip abduction/adduction 13°, hip flexion/extension 140.8°/28.3°, hip rotation 16°
Total height must adjust 13"-22" and total width must adjust 18.07"-25.8"

with the final design for the disclosed exoskeleton—a passive pediatric exoskeleton—containing a ratcheting hip mechanism and a single exotendon from the hip to the ankle.

The disclosed exoskeleton aims to improve over current solutions, which do not adequately meet the needs of pediatric patients.

Design Selection Process

In order to select between the cam and Geneva mechanism designs, initially prototypes were modeled and 3D printed (FIGS. 3A and 3B). The ideal radius for both was optimized using the method described herein. It was determined that the cam design, while low profile, would be difficult to manufacture and assemble due to its small size. On the other hand, the Geneva mechanism is much bulkier than the cam design and requires a higher number of components. The Geneva mechanism was selected as a preferred embodiment because it allows for two-directional ratcheting and improves safety by enclosing the spring. However, in certain embodiments the hip pulley comprises a cam mechanism.

In a preferred embodiment the exoskeleton consists of a hip mechanism containing a Geneva mechanism and torsional spring, a cushioned hip belt, adjustable leg struts, cuffs at mid-thigh and mid-calf, and an ankle pulley. FIG. 1B illustrates the full assembly featuring the bilateral design as was fabricated for testing.

The hip mechanism is an important component of the disclosed exoskeleton. It houses the energy storing torsional spring, which is attached to the exotendon and a Geneva mechanism for adjusting the force. FIG. 3C illustrates a representative Geneva mechanism that converts the continuous rotation of the crank into intermittent rotation using a slot and pin. With this in place, the tension in the spring can be both increased and reduced. Additionally, the housing improves safety as it prevents snagging or pinching in the spring.

The hip belt is critical for anchoring the disclosed exoskeleton to the body and maintains alignment with the legs. The back plate is attached to two side panels, which are curved to comfortably fit the contours of the user's hip bones. Each side panel has a small slot where the hip mechanism can be attached. All three pieces are made from thermoformed high impact polystyrene, for example, to allow some flexibility while maintaining the shape. The belt has removable cushioning for comfort and is secured with a Velcro strap for easy donning and doffing.

Referring again to FIG. 4, in one embodiment the upper and lower leg struts feature a sliding bar 174 between two stationary plates 172 and 180, for example manufactured from 7000 series aluminum to provide high strength at a low weight. A small pin 182 allows for the height to be incrementally adjusted and locked into place. Because the pin 182 is pulled outwards to release rather than pushed in, it is difficult to accidentally trigger during use. Overall, the legs can be adjusted across a 10-inch range, which ensures that the device can grow with a child.

The ankle of the disclosed exoskeleton has an ankle pulley where the exotendon terminates.

The joint can be adjusted by inserting a pin or locking bar that prevents plantarflexion of the ankle joint 108 to prevent foot drop, a common problem in cerebral palsy, if needed. The footplate is also attached at his point, and can either be an over-shoe clinical model or a custom formed in-shoe orthosis for community use.

Prototype Iteration

Initial prototyping of the disclosed exoskeleton was primarily accomplished using 3D printing, laser cutting, machining, and modifying existing parts. The early iterations were used to check the design against any specifications that do not depend on the material, including range of motion and adjustability, as well as evaluated for feasibility or small oversights in the design.

To begin, all parts in the leg struts and joints were initially either 3D printed in PLA (polylactic acid) or laser cut from acrylic. For the first iteration, the main adjustments focused on size of components. The knee joint was found to be significantly too small and would likely have been too weak. Additionally, the holes for fasteners were too close to the edge of the parts and left only a thin strip, which would have failed quickly. After addressing these flaws, the second iteration revealed that the design had not conserved the space needed for screw heads and that the holes needed more space between them to accommodate this. After these changes were made, the parts were produced with a water jet as additional validation required aluminum struts.

Concurrent to the prototyping for main structure of the disclosed exoskeleton, the belt, hip mechanism and cuffs were evaluated. This was largely focused on comfort and fit. For example, determining the appropriate cushion thickness and resizing the cuffs as needed was done during this time.

Manufacturing

A feasible device should be manufactured as easily as possible. To that end, as many parts as possible were designed to be mass produced using conventional manufacturing methods, though some of the parts were made using non-conventional methods for the initial prototype.

All components of the upper and lower leg struts, as well as various internal parts that make up the hip pulley mechanism were designed such that they could be made out of plate material using either a waterjet or laser cutter. These manufacturing methods are ideal for mass productions.

The spring housing and joints have to be CNC machined out of aluminum due to the specific three-dimensional geometries. For interlocking joints, different alloys were used to ensure that both parts would induce wear. If these parts were to be mass-produced, they would be cast in the same material and then post processed to reduce the time and cost required to make them.

Several of the parts used in the prototype were 3D printed in place of the desired method, due to availability and expense. If these parts were mass-produced, some would be heat formed, while others would be injection molded, to decrease manufacturing time and cost. In one embodiment the parts that make up the hip belt and leg cuffs would be heat formed out of high-impact polystyrene (HIPS). In one embodiment the pulleys and enclosure for the Geneva mechanism is injection molded. Utilizing heat forming and injection molding for these parts would severely decrease manufacturing time and cost for mass production, as well as add strength to the parts.

The spiral torsion spring was manufactured by hand, using heat forming, for the exemplary prototype. This was due to the high cost of custom ordering the exact spring. If the exoskeleton were to be mass-produced, the spring could be formed using mass-production methods know to those of skill in the art.

Performance Testing

The disclosed exoskeleton was tested to validate that the design meets the design specifications and core function. These tests include adjustability and range of motion tests, a 3-point bend test on the knee joint, a pendulum test for acceleration, a scratch test for safety, and a preliminary comfort and fit test.

Range of Motion & Adjustability.

Both range of motion and adjustability were tested by manually moving the device and measuring the minimum and maximum values. For adjustability, the design specification required 9 inches (228.6 mm) for vertical adjustment as well as 8 inches (203.2 mm) of adjustment around the waist. The exoskeleton was measured in both its shortest and tallest configurations to confirm the leg struts will accommodate the desired range of patients and found to allow 9.67 inches (245.6 mm) of change (Table 2). The hip belt was not tested for circumferential range of motion because it was prototyped out a of a much more rigid material than designed for. The angular ranges of motion allowed at each joint are recorded in Table 3. Though the disclosed exoskeleton slightly restricts the motion in many directions, it more than allows for the range needed during both walking and sitting.

TABLE 2

Experimental leg-segment adjustability.

| | |
|---|---|
| Shortest tibia length (ankle center to knee center) | 183.0 mm |
| Shortest femur length (knee center to screw connecting the hip pulley to ball joint) | 196.0 mm |
| Longest tibia length | 289.0 mm |
| Longest femur length | 345.0 mm |

TABLE 3

Experimental angular range of motion at the knee and hip joint.

| Joint | Type of Motion | Average Unimpaired Range (Children 2-8) | Disclosed Exoskeleton Range |
|---|---|---|---|
| Hip Joint | Flexion | 136° | 106° |
| | Extension | 28° | 109° |
| | Rotation | 16° | 360° |
| | Abduction | 13° | 10° |
| | Adduction | 13° | 10° |
| Knee Joint | Flexion | 150° | 107° |
| | Extension | 4° | 0° |

Pendulum Test.

A pendulum test was conducted to confirm that the disclosed exoskeleton does not prevent an unimpaired gait, either through jerk during the swing phase of walking or overall reducing tibial accelerations. Although the device is passive, it was important to ensure that the user would not be working against the device while walking. The test was conducted by attaching an accelerometer to the ankle of the disclosed exoskeleton while it was weighted to simulate either a 3-year or 6-year old user, by adding weights of approximately 1.5 lbs. and 3.6 lbs. respectively. Including testing equipment, the total weights added were 1.43 lbs. and 3.88 lbs. The hip and thigh were secured in a horizontal position; the lower leg was extended into a straightened position and released to swing freely (FIGS. 5A-5D). With the positioning of the acceleration, the x-axis measured proximal/distal motion, the y-axis measured anterior/posterior motion, and the z-axis measured medial/lateral motion.

Figure 5A:
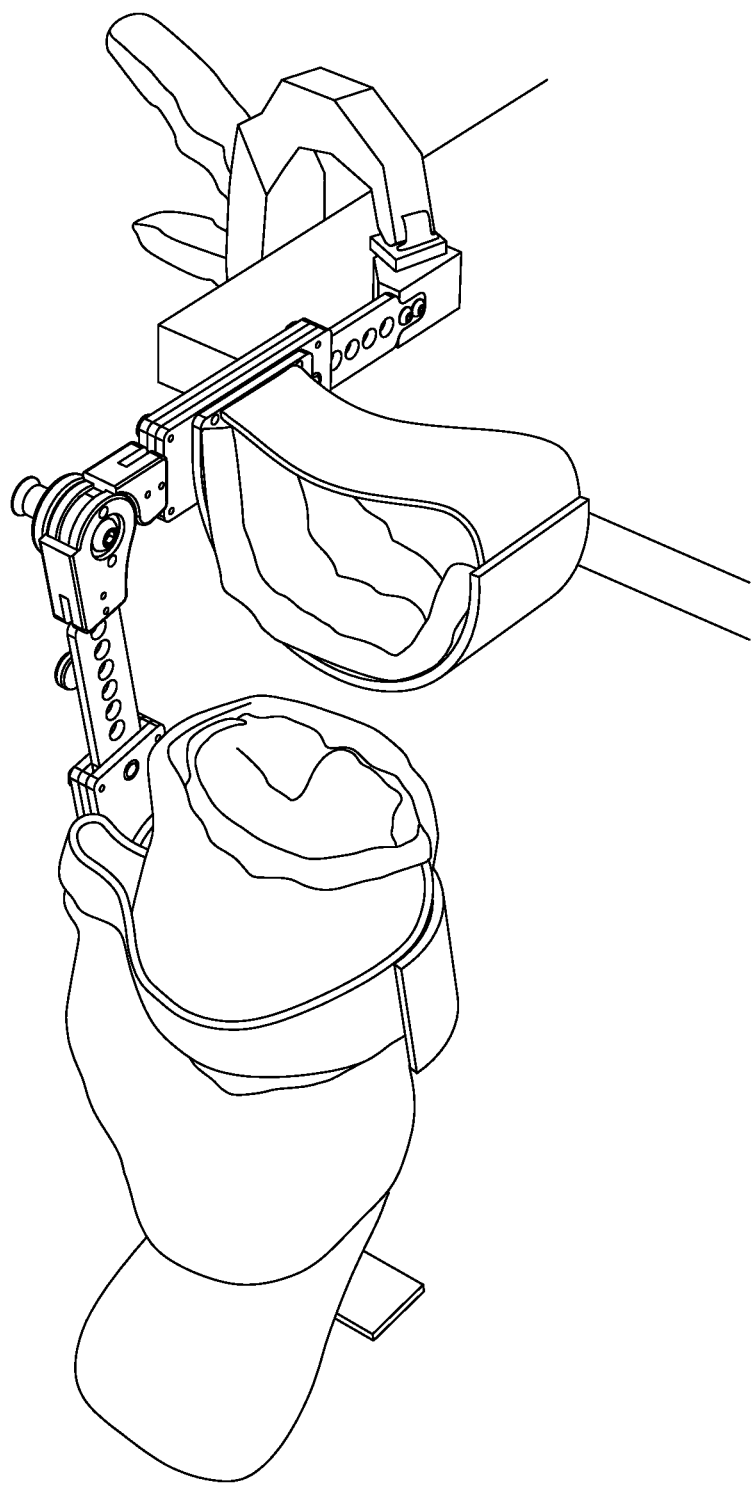
FIGS. 5A-5D: A pendulum test for an exemplary leg exoskeleton.
Figure 5B:
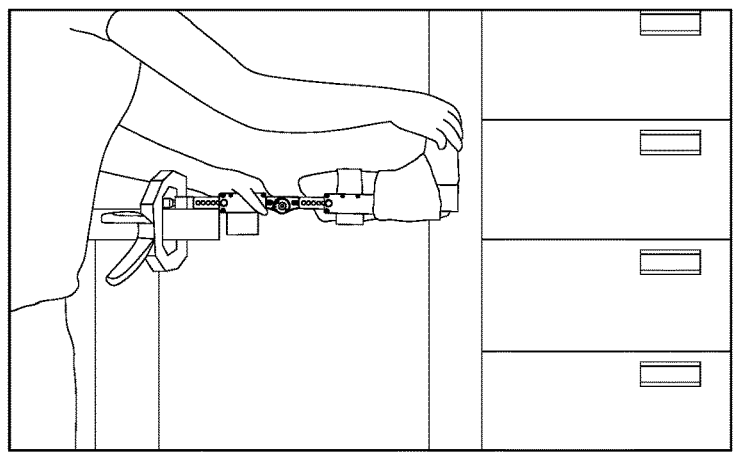
Figure 5C:
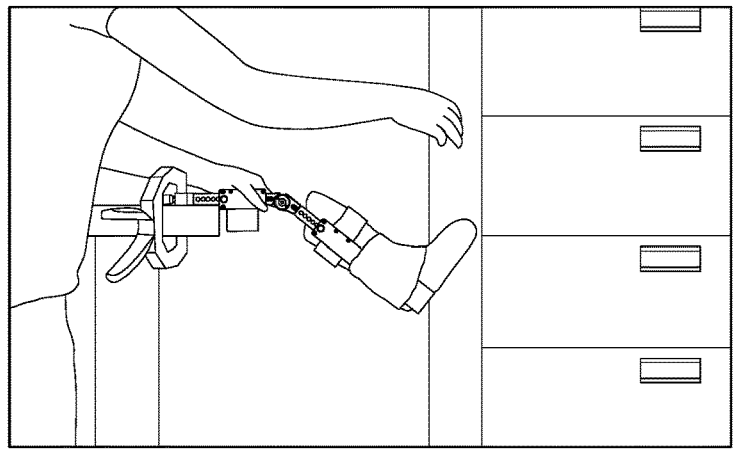
Figure 5D:
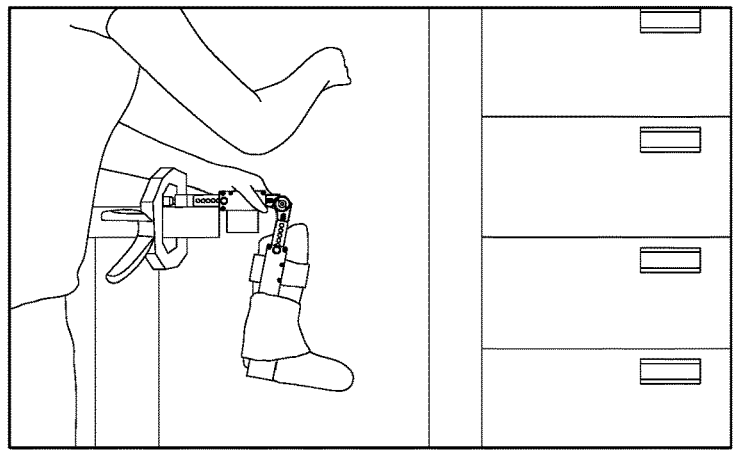

FIG. 5A: Testing configuration with the thigh strut fixed to the table and the foot and tibia free to swing about the knee joint. FIG. 5B: The leg completely extended, preparing to release. FIG. 5C: The foot freely swinging. FIG. 5D: The foot at rest after the pendulum test.

In Table 4 below, the peak tibial accelerations recorded during the pendulum test are provided along with the design specifications as determined by an adult male walking in shod conditions. The anterior-posterior peak accelerations shown for the 3- and 6-year old bottom out at −2 g which is most likely an issue with the accelerometer and not actually the true acceleration values.

The anterior-posterior peak accelerations show that the disclosed exoskeleton weighted with a 3- and 6-year old foot meets design specification of −2.09 g. The disclosed exoskeleton weighted with a 3-year old foot allow motion greater than needed but not when weighted with a six-year old foot. The axial accelerations of allowed by the disclosed exoskeleton are slightly restricted compared to the 1.70 g in the design specification. Though this test does not fully demonstrate that the disclosed exoskeleton promotes fluid movement by not impeding the acceleration of typical gait, this was a limitation of the test setup rather than the device.

TABLE 4

Tibial acceleration results from the pendulum test.

|  | Anterior-Posterior Peak Negative Accel (g) (Y) | Lateral Peak Positive Accel (g) (Z) | Axial Peak Accel (g) (X) |
|---|---|---|---|
| Adult male (design specification) | −2.09 | 0.90 | 1.70 |
| Three year old | −2 | 1.4385 | 1.3560 |
| Six year old | −2 | 0.5387 | 1.2784 |

3-Point Bend Test.

Figure 6:
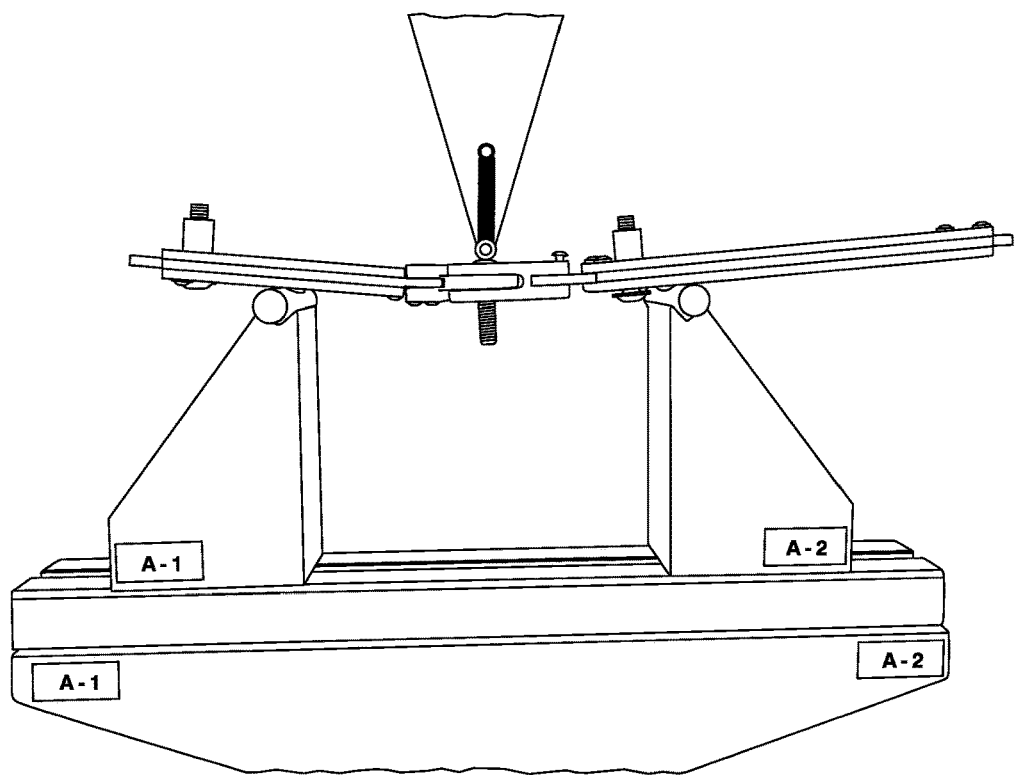
FIG. 6: 3-point bend test configuration with the loading applied laterally at the knee joint.

In order to ensure that the disclosed exoskeleton will not fail at the knee and cause injury to the wearer, the knee joint was tested until failure in 3-point loading, as illustrated in FIG. 6. The test was conducted on a partially assembled leg, consisting of an upper leg strut, knee joint, and lower leg strut. The assembly was placed with the force applied laterally to the center of the knee and with the supports located 65 mm to the left and right. Because the test is meant to evaluate the knee, the supports were placed fairly close, rather than at the end of the struts. The load was applied at a rate of 3 mm per minute until failure occurred.

Figure 7:
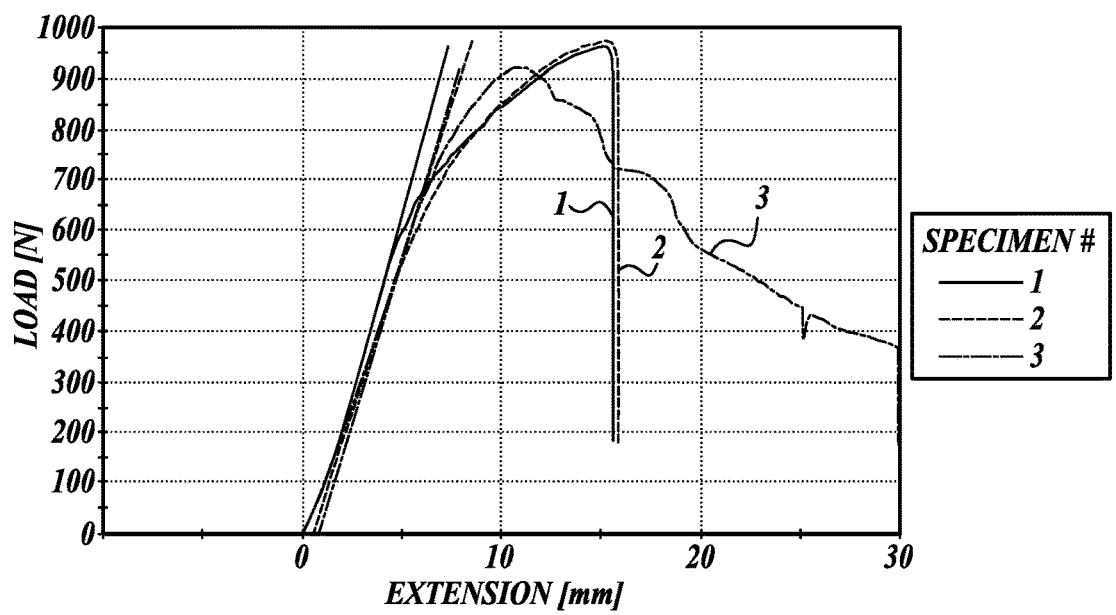
FIG. 7: Load vs. extension curve for the three knee joints tested in the 3-point bend test.

The results are illustrated in FIG. 7 (load vs. extension curve for the three knee joints tested in the 3-point bend test), and in all cases the force required for both plastic deformation and failure vastly exceeded any force the device would experience under typical wear. The failure occurred not in the knee joint, but at the small tab connecting the strut to the knee. Possible sources for data errors are most likely inconsistencies in the parts in either tolerances or friction.

Fit and Comfort.

For fit and comfort, the final prototype was worn by an unimpaired five-year-old child, as illustrated in FIGS. 8A and 8B. After adjusting the device to fit properly, she was asked if anything was hurting or felt bad. In order to observe how the device shifted during movement, she also walked across the room several times. This test demonstrated that the disclosed exoskeleton does adjust to fit this specific size and does not hurt the patient. It also revealed small adjustments still needed in the cuff and belt placement to keep the device secured to the body before moving forward with clinical trials.

While illustrative embodiments have been illustrated and described, it will be appreciated that various changes can be made therein without departing from the spirit and scope of the invention.

The embodiments of the invention in which an exclusive property or privilege is claimed are defined as follows:

1. A leg exoskeleton comprising:
   a belt configured to attach to a user, the belt comprising a hip attachment mechanism configured for removably coupling a leg frame to a hip of the user;
   the leg frame having a proximal portion and a distal portion, the leg frame configured for extending along a length of the user's leg when the user dons the leg exoskeleton with the proximal portion coupled to the hip attachment mechanism at a hip joint and the distal portion coupled to the user at a location distal to the user's knees; and
   an energy storage subsystem coupled to the hip attachment mechanism and the leg frame, the energy storage subsystem comprising:
      an exotendon extending from the hip attachment to the distal portion of the leg frame, the exoskeleton configured to store energy as the user's leg moves posteriorly and release stored energy to aid the user with moving the leg anteriorly,
      a biasing member disposed along the exotendon, the biasing member configured for storing and releasing energy, and
      a two-way ratchet disposed along the exotendon in proximity to the hip attachment mechanism, the two-way ratchet configured for adjusting tension in the exotendon via biasing member, and
      wherein the biasing member is disposed at least partially within a housing that contains the two-way ratchet.

2. The leg exoskeleton of claim 1, wherein the two-way ratchet is a Geneva mechanism.

3. The leg exoskeleton of claim 1, wherein the biasing member is a spring disposed within the housing.

4. The leg exoskeleton of claim 3, wherein the spring is a spiral torsion spring.

5. The leg exoskeleton of claim 4, wherein the spiral torsion spring is entirely enclosed within a case enclosing the biasing member.

6. The leg exoskeleton of claim 1, wherein the leg frame has an adjustable length.

7. The leg exoskeleton of claim 1, further comprising a knee pulley disposed adjacent a knee joint of the leg frame, the knee pulley being configured to guide the exotendon between the proximal portion and the distal portion of the leg frame.

8. The leg exoskeleton of claim 1, further comprising an ankle pulley disposed on the distal portion of the leg frame and configured to secure a distal end of the exotendon.

9. The leg exoskeleton of claim 1, wherein the leg frame further comprises a knee pulley and an ankle pulley.

10. The leg exoskeleton of claim 1, wherein the leg frame is releasably secured to the hip attachment mechanism.

11. The leg exoskeleton of claim 10, wherein the releasably secured leg frame is attached to the hip attachment mechanism by a spring-loaded system that requires pushing on two tabs to release the leg frame from the hip attachment mechanism.

12. The leg exoskeleton of claim 1, wherein the leg frame is a first leg frame configured for extending along a length of the user's first leg, and wherein the leg exoskeleton comprises a second leg frame configured for extending along a length of the user's second leg.

13. The leg exoskeleton of claim 12, wherein the energy-storage subsystem is a first energy-storage subsystem coupled to the hip attachment mechanism and the first leg frame, and wherein the leg exoskeleton comprises a second energy-storage subsystem coupled to the hip attachment mechanism and the second leg frame.

14. A method of using the leg exoskeleton of claim 1, the method comprising:
   attaching the leg exoskeleton to at least one leg of a user; and
   assisting the user in movement of the at least one leg.

15. The method of claim 14, wherein assisting the user in movement of the at least one leg comprises storing energy in the biasing member when the at least one leg swings posteriorly during walking and releasing energy from the biasing member when the at least one leg swings anteriorly during walking, thereby assisting the user with movement forward.

16. The method of claim 14, further comprising pre-biasing the biasing member so as to provide stored energy in the biasing member before any movement of the user.

17. The method of claim 14, wherein the leg exoskeleton is attached to two legs of the user and assists in movement of the two legs.

18. The method of claim 14, further comprising adjusting the length of the leg frame in order to fit the user prior to movement.

19. The method of claim 14, wherein the biasing member comprises a spiral torsion spring attached to the proximal end of the exotendon.

\* \* \* \* \*